(12) United States Patent
Tsubata

(10) Patent No.: US 10,119,936 B2
(45) Date of Patent: Nov. 6, 2018

(54) ELECTROMAGNETIC FIELD ANALYSIS METHOD FOR ANISOTROPIC CONDUCTIVE MATERIAL

(71) Applicant: Fuji Jukogyo Kabushiki Kaisha, Tokyo (JP)

(72) Inventor: Hiroyuki Tsubata, Tokyo (JP)

(73) Assignee: SUBARU CORPORATION, Tokyo (JP)

( * ) Notice: Subject to any disclaimer, the term of this patent is extended or adjusted under 35 U.S.C. 154(b) by 0 days.

(21) Appl. No.: 15/417,085

(22) Filed: Jan. 26, 2017

(65) Prior Publication Data

US 2017/0284964 A1    Oct. 5, 2017

(30) Foreign Application Priority Data

Mar. 31, 2016   (JP) .................................. 2016-069876

(51) Int. Cl.
*G01N 27/60*          (2006.01)

(52) U.S. Cl.
CPC .................................... *G01N 27/60* (2013.01)

(58) Field of Classification Search
CPC ......... G01N 27/60; G06F 1/137; G06F 17/50; G06F 17/5009; G06F 17/5018; G06F 17/5036; G06F 17/5095; G06F 17/10; G06F 17/11; G06F 17/40; G06F 2217/16; G06F 2217/12; G06F 2217/44; G01R 29/0814; G02B 5/3083
See application file for complete search history.

(56) References Cited

U.S. PATENT DOCUMENTS

| | | | |
|---|---|---|---|
| 6,700,368 B2 * | 3/2004 | Takano | G06F 17/5018 324/210 |
| 7,248,041 B2 * | 7/2007 | Manring | G01R 33/123 324/228 |
| 2005/0024048 A1 * | 2/2005 | Manring | G01R 33/123 324/239 |

(Continued)

FOREIGN PATENT DOCUMENTS

JP        2001-183404 A        7/2001

OTHER PUBLICATIONS

Extended European Search Report dated Aug. 18, 2017 in European Application No. 17157394.2.

(Continued)

*Primary Examiner* — Thang Le
(74) *Attorney, Agent, or Firm* — McGinn, I.P. Law Group, PLLC.

(57) ABSTRACT

An electromagnetic field analysis method for an anisotropic conductive material involves using an analysis grid having a first side and a second side that are orthogonal to each other to analyze an electromagnetic property of an anisotropic conductive material in which conductivity in a first direction is different from conductivity in a second direction. One or both of the first direction and the second direction are parallel to a direction different from either one of the first side and the second side of the analysis grid. One electromagnetic field component located on the first side and extending along the second side is calculated based on electromagnetic field components that are located on a plurality of the second sides surrounding the one electromagnetic field component and that extend along the second sides.

18 Claims, 2 Drawing Sheets

(56) References Cited

U.S. PATENT DOCUMENTS

| | | |
|---|---|---|
| 2007/0219762 A1* | 9/2007 | Odajima ............ G06F 17/5009 703/2 |
| 2009/0055121 A1 | 2/2009 | Kiso |
| 2010/0280778 A1* | 11/2010 | Ohta .................. G06F 17/5018 702/66 |
| 2011/0238196 A1 | 9/2011 | Takahashi et al. |
| 2015/0142397 A1 | 5/2015 | Pond |

OTHER PUBLICATIONS

Japanese Office Action dated Nov. 7, 2017 in Japanese Application No. 2016-069876 with an English translation thereof.
Miyake, et al., "Development of EMC measurement method against instruments onboard spacecraft with FDTD simulations." The Toyama Prefectural University Bulletin, Mar. 30, 2007, vol. 17, pp. 61-69 (with English Abstract).

* cited by examiner

ELECTROMAGNETIC FIELD ANALYSIS METHOD FOR ANISOTROPIC CONDUCTIVE MATERIAL

CROSS-REFERENCE TO RELATED APPLICATIONS

The present application claims priority from Japanese Patent Application No. 2016-069876 filed on Mar. 31, 2016, the entire contents of which are hereby incorporated by reference.

BACKGROUND

1. Technical Field

The present invention relates to electromagnetic field analysis methods for anisotropic conductive materials having anisotropic conductivity.

2. Related Art

When designing airframes of aircrafts, countermeasures against lightning are necessary for preventing, for instance, fuel ignition occurring from sparks caused by lightning strikes. With regard to such a countermeasure against lightning, it is important to clarify the electric current distribution within the airframe when struck by lightning. In order to achieve this, a highly-accurate electromagnetic field analysis method is desired.

With regard to an electromagnetic field analysis method of this kind, a finite-difference time-domain (FDTD) method is widely used (for instance, see Japanese Unexamined Patent Application Publication No. 2001-183404). The FDTD method involves calculating electromagnetic field components (i.e., electric field and magnetic field) along three orthogonal axes by using a cubical analysis grid called a Yee grid.

As a structural material for the airframe of an aircraft, a composite material, such as carbon fiber reinforced plastic (CFRP) with high specific strength, is being put to practical use. When performing an electromagnetic field analysis of such a composite material, since each fiber is electrically conductive, the anisotropic conductivity in the fiber direction has to be taken into consideration.

A known analysis method in the related art that deals with anisotropic conductivity involves the use of conductivity tensor representation.

In this analysis method, the anisotropic conductivity is expressed by an off-diagonal element of a conductivity tensor occurring when the conductivity defined on a three-orthogonal-axes coordinate system is rotated about a z-axis. Then, the conductivity tensor is applied to Maxwell's equation, and a finite difference method is used, whereby a discretized expression is obtained for each axis.

In the definition of a Yee grid, electromagnetic fields of the respective discretized axes are located at different positions in the grid. However, the obtained discretized expression has a mixture of electromagnetic fields at different positions (i.e., electromagnetic fields at positions not defined in the Yee grid). Thus, the calculation cannot be performed with the expression in this state (this will be described later in detail in the implementation). In the analysis method in the related art, the analysis is attempted based on an assumption that these electric fields at different positions are identical to each other.

However, simply defining these electric fields at different positions as being identical to each other, as in the above-described analysis method in the related art, leads to reduced approximation accuracy.

SUMMARY OF THE INVENTION

It is desirable to perform an electromagnetic field analysis of an anisotropic conductive material having anisotropic conductivity with higher accuracy than in the related art.

An aspect of the present invention provides an electromagnetic field analysis method for an anisotropic conductive material, in which an analysis grid having a first side and a second side that are orthogonal to each other is used to analyze an electromagnetic property of an anisotropic conductive material in which conductivity in a first direction is different from conductivity in a second direction. One or both of the first direction and the second direction are parallel to a direction different from either one of the first side and the second side of the analysis grid, and one electromagnetic field component located on the first side and extending along the second side is calculated based on electromagnetic field components that are located on the second sides surrounding the one electromagnetic field component and that extend along the second sides.

The one electromagnetic field component may be calculated as an average value of the electromagnetic field components.

In a case where the one electromagnetic field component is located on the first side extending along a peripheral edge of the anisotropic conductive material, the one electromagnetic field component may be calculated based on any of the electromagnetic field components included in the anisotropic conductive material.

The analysis grid may be a cubical analysis grid extending along three orthogonal axes. The electromagnetic field components may include four electromagnetic field components respectively located on four of the second sides coupled to the first side at two nodal points of opposite ends of the first side on which the one electromagnetic field component is located.

The electromagnetic field analysis method may use a finite-difference time-domain method. The analysis grid may be a cubical analysis grid extending along three orthogonal axes. A conductivity tensor obtained when conductivity defined in a coordinate system of the three orthogonal axes is rotated about an axis orthogonal to both of the first direction and the second direction may be applied to Ampere's expression and may subsequently be discretized by using a finite difference method. When performing calculation repeatedly by applying an iterative method to the discretized expression, an undefined electromagnetic field component included in the discretized expression may be calculated as the one electromagnetic field component from the electromagnetic field components.

In the electromagnetic field analysis method according to the above aspect, the anisotropic conductive material may be fiber reinforced plastic in which plastic is reinforced with conductive fiber extending in either one of the first direction and the second direction.

DETAILED DESCRIPTION

Figure 1A:
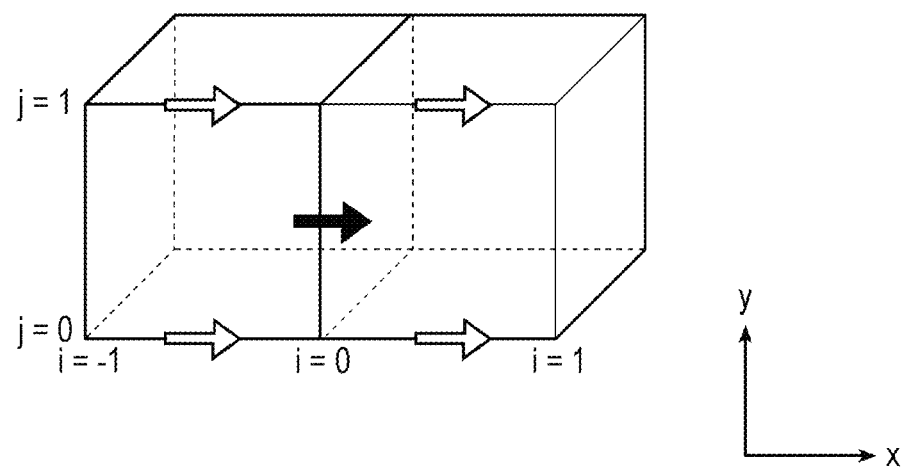
FIGS. 1A and 1B illustrate calculation methods for determining an undefined electromagnetic field component from a plurality of defined electromagnetic field components.

An implementation of the present invention will be described below with reference to the drawings.

In an electromagnetic field analysis method for an anisotropic conductive material (simply referred to as "electromagnetic field analysis method" hereinafter) according to this implementation, the electromagnetic property, such as the electric current distribution, of a material having anisotropic conductivity is calculated by using a finite-difference time-domain (FDTD) method. The FDTD method is a numerical analysis method that involves calculating electromagnetic field components along three orthogonal axes by using a cubical analysis grid (Yee grid) in which the respective sides extend along three orthogonal xyz axes.

The anisotropic conductive material being analyzed has anisotropic conductivity in which the conductivity in a certain direction differs from that in another direction. In this implementation, the anisotropic conductive material is fiber reinforced plastic (FRP) in which plastic is reinforced with conductive fibers. In such FRP, the conductivity in the fiber direction is higher than that in another direction, so that electric current flows readily in the fiber direction.

In the electromagnetic field analysis method according to this implementation, an analysis technique using anisotropic-conductivity tensor representation is employed.

This analysis technique will be described in detail below.

In view of a state where the object being analyzed is rotated about an axis orthogonal to the fiber direction, the anisotropic conductivity in the direction different from the three orthogonal axes can be derived by using a relational expression of a current density J and an electric field E expressed with expression (1) below and rotating the current density and the electric field about the z-axis by an angle θ, as in expression (2) below. Each underlined part in expression (3) obtained by modifying expression (2) is an off-diagonal element of a conductivity tensor. This off-diagonal element is zero when θ=0.

$$J = \sigma E \quad (1)$$

$$\begin{bmatrix} \cos\theta & \sin\theta \\ -\sin\theta & \cos\theta \end{bmatrix} \begin{bmatrix} J_x \\ J_y \end{bmatrix} = \begin{bmatrix} \sigma_p & 0 \\ 0 & \sigma_t \end{bmatrix} \begin{bmatrix} \cos\theta & \sin\theta \\ -\sin\theta & \cos\theta \end{bmatrix} \begin{bmatrix} E_x \\ E_y \end{bmatrix} \quad (2)$$

$$\begin{bmatrix} J_x \\ J_y \end{bmatrix} = \begin{bmatrix} \sigma_p\cos^2\theta + \sigma_t\sin^2\theta & \underline{(\sigma_p - \sigma_t)\cos\theta\sin\theta} \\ \underline{(\sigma_p - \sigma_t)\cos\theta\sin\theta} & \sigma_t\cos^2\theta + \sigma_p\sin^2\theta \end{bmatrix} \begin{bmatrix} E_x \\ E_y \end{bmatrix} \quad (3)$$

In this case, $\sigma_p$ denotes the conductivity in the fiber direction, and $\sigma_t$ denotes the conductivity in a direction orthogonal to the fiber direction within the x-y plane.

The conductivity of the material having anisotropy in any direction within the x-y plane can be expressed with expression (4) below, assuming that components $\sigma_{xx}$, $\sigma_{yy}$, and $\sigma_{zz}$ correspond to the respective axial directions and off-diagonal elements mentioned above are denoted by $\sigma_{xy}$, and $\sigma_{yx}$.

$$\sigma = \begin{bmatrix} \sigma_{xx} & \sigma_{xy} & 0 \\ \sigma_{yx} & \sigma_{yy} & 0 \\ 0 & 0 & \sigma_{zz} \end{bmatrix} \quad (4)$$

In order to directly solve Maxwell's equation in the FDTD method, expression (6) below is obtained by applying expression (4) to Ampere's expression (5) in Maxwell's equation.

$$\nabla \times H = \varepsilon \frac{\partial E}{\partial t} + \sigma E \quad (5)$$

$$\begin{cases} \frac{\partial H_z}{\partial y} - \frac{\partial H_y}{\partial z} = \varepsilon \frac{\partial E_x}{\partial t} + \sigma_{xx} E_x + \sigma_{xy} E_y \\ \frac{\partial H_x}{\partial z} - \frac{\partial H_z}{\partial x} = \varepsilon \frac{\partial E_y}{\partial t} + \sigma_{yx} E_x + \sigma_{yy} E_y \\ \frac{\partial H_y}{\partial x} - \frac{\partial H_x}{\partial z} = \varepsilon \frac{\partial E_z}{\partial t} + \sigma_{zz} E_z \end{cases} \quad (6)$$

In expression (6), each parameter is satisfied at any one point in a three-dimensional space. However, in the definition of a Yee grid in the FDTD method, discretized components $E_x$, $E_y$, and $E_z$ exist at different positions in the analysis grid. The electric field in the Yee grid is located in an area corresponding to the sides of the grid, and the components $E_x$, $E_y$, and $E_z$ are located on different sides (i.e., sides extending along the respective axes) of each grid. In discretization, the position of the electric field has to be clarified.

By denoting the position of the electric field as "|i, j, k" and discretizing expression (6) using a finite difference method, expression (7) to expression (9) below are obtained.

$$E_x^n|_{i+\frac{1}{2},j,k} = k_{1x} E_x^{n-1}|_{i+\frac{1}{2},j,k} + k_{xy}\left(E_y^n|_{i+\frac{1}{2},j,k} + E_y^{n-1}|_{i+\frac{1}{2},j,k}\right) + \quad (7)$$

$$k_{2x}\frac{H_z^{n-1}|_{i+\frac{1}{2},j+\frac{1}{2},k} - H_z^{n-1}|_{i+\frac{1}{2},j-\frac{1}{2},k}}{\Delta y} +$$

$$k_{2x}\frac{H_y^{n-1}|_{i+\frac{1}{2},j,k+\frac{1}{2}} - H_y^{n-1}|_{i+\frac{1}{2},j,k-\frac{1}{2}}}{\Delta z}$$

$$E_y^n|_{i,j+\frac{1}{2},k} = k_{1y} E_y^{n-1}|_{i,j+\frac{1}{2},k} + k_{yx}\left(E_x^n|_{i,j+\frac{1}{2},k} + E_x^{n-1}|_{i,j+\frac{1}{2},k}\right) + \quad (8)$$

$$k_{2y}\frac{H_x^{n-1}|_{i,j+\frac{1}{2},k+\frac{1}{2}} - H_x^{n-1}|_{i,j+\frac{1}{2},k-\frac{1}{2}}}{\Delta z} +$$

$$k_{2y}\frac{H_z^{n-1}|_{i+\frac{1}{2},j+\frac{1}{2},k} - H_z^{n-1}|_{i-\frac{1}{2},j+\frac{1}{2},k}}{\Delta x}$$

$$E_z^n|_{i,j,k} = k_{1z} E_z^{n-1}|_{i,j,k} + k_{2z}\frac{H_y^{n-1}|_{i+\frac{1}{2},j,k+\frac{1}{2}} - H_y^{n-1}|_{i-\frac{1}{2},j,k+\frac{1}{2}}}{\Delta x} + \quad (9)$$

$$k_{2z}\frac{H_x^{n-1}|_{i,j+\frac{1}{2},k+\frac{1}{2}} - H_x^{n-1}|_{i,j-\frac{1}{2},k+\frac{1}{2}}}{\Delta y}$$

In expression (7) and expression (8), there is a mixture of electric fields at different positions. Specifically, in a Yee grid, there is a component $E_x$ (referred to as "undefined component $E_x$" hereinafter) located on a side where the component $E_x$ is not defined (i.e., the side where a component $E_y$ is defined along the y-axis), and a component $E_y$ (referred to as "undefined component $E_y$" hereinafter) located on a side where the component $E_y$ is not defined (i.e., the side where the component $E_x$ is defined along the x-axis). Therefore, the calculations cannot be performed using the expressions in these states.

With respect to this problem, the analysis technique in the related art simultaneously uses expression (7) and expression (8), assuming that these electric fields at different positions are identical to each other, as in expression (10) below.

$$\begin{cases} E_x^n \big|_{i,j+\frac{1}{2},k} = E_x^n \big|_{i+\frac{1}{2},j,k} \\ E_y^n \big|_{i+\frac{1}{2},j,k} = E_y^n \big|_{i,j+\frac{1}{2},k} \end{cases} \quad (10)$$

However, defining these electric fields at different positions as being identical to each other leads to reduced approximation accuracy.

Figure 1B:
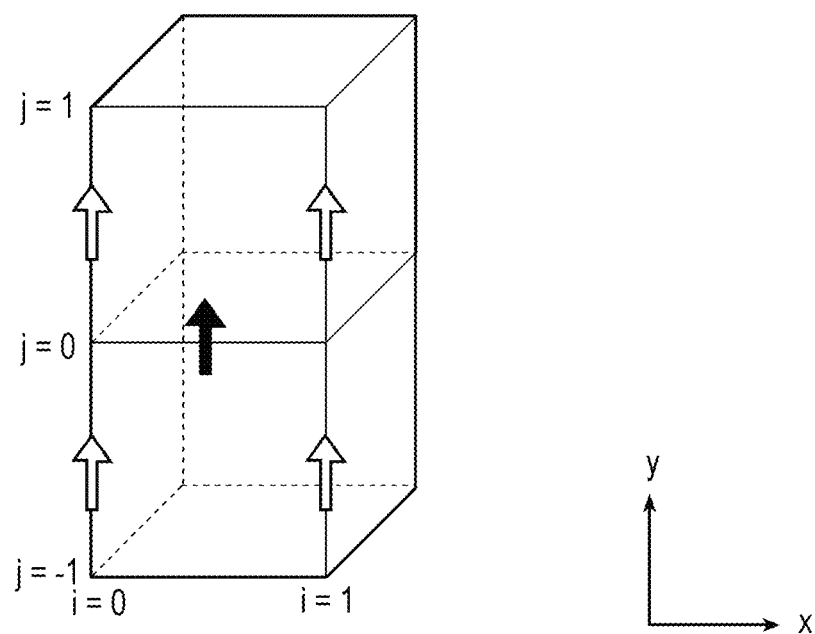

As illustrated in FIG. 1A, the electromagnetic field analysis method according to this implementation does not use the assumption based on expression (10) above but approximates the value of the undefined component $E_x$ (indicated by a solid arrow in FIG. 1A) as an average value of four components $E_x$ (indicated by voided arrows in FIG. 1A), which are components $E_x$ that are located on sides where the components $E_x$ are defined (referred to as "defined components $E_x$" hereinafter) and that are located on four sides surrounding the undefined component $E_x$. Furthermore, the same applies to the component $E_y$. Specifically, as illustrated in FIG. 1B, similar to the case of the component $E_x$, the value of the undefined component $E_y$ is approximated as an average value of four components $E_y$, which are components $E_y$ that are located on sides where the components $E_y$ are defined (referred to as "defined components $E_y$" hereinafter) and that are located on four sides surrounding the undefined component $E_y$.

In detail, the undefined component $E_x$ and the undefined component $E_y$ are calculated using expression (11) and expression (12) below.

$$E_x^n \big|_{i,j+\frac{1}{2},k} = \frac{E_x^n \big|_{i+\frac{1}{2},j,k} + E_x^n \big|_{i+\frac{1}{2},j+1,k} + E_x^n \big|_{i-\frac{1}{2},j,k} + E_x^n \big|_{i-\frac{1}{2},j+1,k}}{4} \quad (11)$$

$$E_y^n \big|_{i+\frac{1}{2},j,k} = \frac{E_y^n \big|_{i,j+\frac{1}{2},k} + E_y^n \big|_{i+1,j+\frac{1}{2},k} + E_y^n \big|_{i,j-\frac{1}{2},k} + E_y^n \big|_{i+1,j-\frac{1}{2},k}}{4} \quad (12)$$

However, if the undefined component $E_x$ is located on a side extending along a peripheral edge of the object being analyzed (i.e., the boundary with the peripheral space), only two defined components $E_x$ (within the boundary), included in the object being analyzed, of the four defined components $E_x$ to be averaged out are used to calculate the undefined component $E_x$, and the values of the two remaining defined components $E_x$ included in the peripheral space are not used.

For instance, in FIG. 1A, in a case where the right analysis grid is included in the object being analyzed and the left analysis grid belongs to the peripheral space, only two defined components $E_x$ of i+½ are used for calculating the undefined component $E_x$.

The same applies to the undefined component $E_y$.

The undefined component $E_x$ may be calculated based on a plurality of surrounding defined components $E_x$, and the method of interpolating the undefined component $E_x$ from the positions and the number of defined components $E_x$ and from a plurality of defined components $E_x$ is not limited to that described above.

If expression (11) and expression (12) above are substituted into expression (7) and expression (8), there would be eight unknowns for $E_x$ and $E_y$. By applying them to various locations on the analysis grids and simultaneously applying them in the entire analytic space to configure a matrix, an analysis is possible.

However, in this implementation, an iterative method, as typified by the Gauss-Seidel method, is applied as a more efficient method, instead of simultaneously using expression (7) and expression (8), such that the calculation is performed repeatedly until the rates of change of the components $E_x$ and $E_y$ become sufficiently small (lower than or equal to a predetermined threshold value). Then, during this repeated calculation process, the undefined components $E_x$ and $E_y$ are interpolated, as appropriate, with a plurality of components $E_x$ and $E_y$ by using expression (11) and expression (12).

Consequently, the electromagnetic property of the anisotropic conductive material can be analyzed.

Analytic Example

Next, an analytic example using the electromagnetic field analysis method according to this implementation will be described.

In this analytic example, the electromagnetic field analysis method according to this implementation is compared with the above-described analysis method in the related art to study the validity of the two methods.

Analytic Model

Figure 2A:
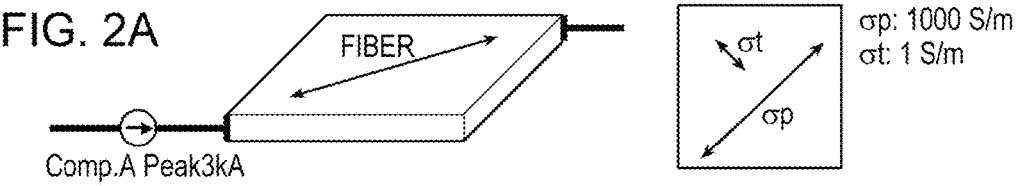
FIG. 2A illustrates an analytic model in an analytic example.

An analytic model used for performing the comparison is a unidirectional-material flat plate, as illustrated in FIG. 2A. This flat plate has a size of 300 mm by 300 mm by 10 mm, and the number of mesh is 21×21×1.

Analysis Conditions

A metal rod defined by a single line on a grid is coupled to an object being analyzed and an absorption boundary so as to define the metal rod as an electrode. An applicator electrode and a return electrode are coupled to opposite ends of the flat plate on a diagonal line thereof that is parallel to the fiber direction.

The applied current has a peak value of 3 kA in a waveform of component A for an aircraft lightning test regulated under SAE ARP-5416.

Although the current density is calculated in this analytic example, the current density to be determined in the electromagnetic field analysis method according to this implementation has to be calculated in view of the effect of an off-diagonal element of a conductivity tensor, as indicated in expression (13) and expression (14) below.

$$J_x = \sigma_{xx}E_x + \sigma_{xy}E_y \quad (13)$$

$$J_y = \sigma_{yx}E_x + \sigma_{yy}E_y \quad (14)$$

Because the electric field in a Yee grid is located in an area corresponding to the sides of each grid, the current density, which is the calculation result described above, is a value at each side of the grid. The current density in each cell is calculated as an average value of current densities surrounding the cell.

Analysis Result

Figure 2B:
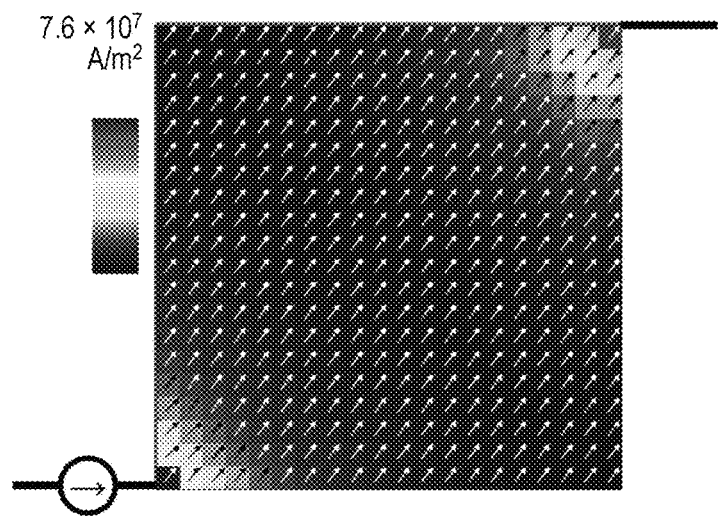
FIG. 2B illustrates an analysis result obtained in accordance with an analysis method in the related art.
Figure 2C:
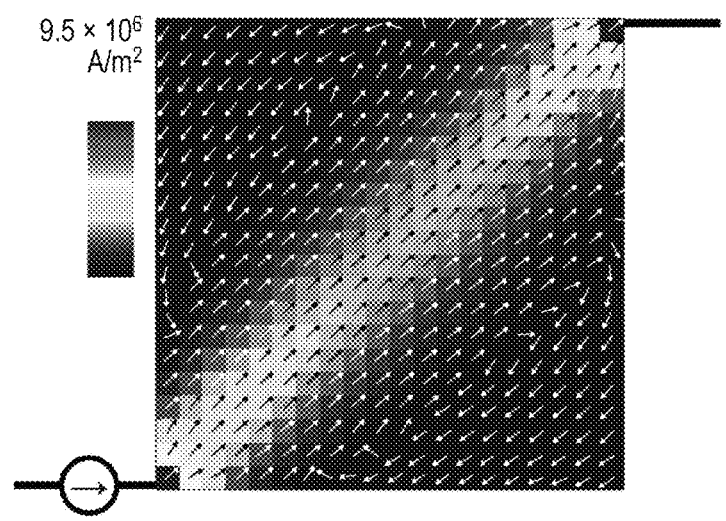
FIG. 2C illustrates an analysis result obtained in accordance with an electromagnetic field analysis method according to an implementation.

FIGS. 2B and 2C illustrate results of this analytic example and illustrate the current density after 6.4 μs at which the applied current reaches the peak value. Specifically, FIG. 2B corresponds to the analysis method in the related art, whereas FIG. 2C corresponds to the electromagnetic field analysis method according to this implementation.

Each analysis result indicates the electric current distribution displayed by filling in the cells formed by the analysis grid using color gradation. In order to display the direction in which the electric current flows in each cell, the vector directions formed by components $J_x$ and $J_y$ in expression (12) and expression (13) are indicated by arrows.

As illustrated in FIG. 2B, in the analysis method in the related art, the current direction in each cell is parallel to the fiber direction, but current concentration caused by anisotropy cannot be calculated.

In contrast, as illustrated in FIG. 2C, in the electromagnetic field analysis method according to this implementation, strong electric current distribution is calculated on the diagonal line of the flat plate in a manner such as to couple the two electrodes to each other. Thus, it can be considered that electric current distribution according to the anisotropic conductivity in the fiber direction is reproduced.

Effects

Accordingly, in the electromagnetic field analysis method according to this implementation, an undefined component $E_x$ located on a side extending along the y-axis of the analysis grid is calculated based on a plurality of defined components $E_x$ surrounding the undefined component $E_x$ and located on sides extending along the x-axis, and an undefined component $E_y$ is similarly calculated based on a plurality of defined components $E_y$.

In other words, the undefined components $E_x$ and $E_y$ are calculated by interpolation based on the plurality of surrounding defined components $E_x$ and $E_y$.

Therefore, as compared with the related art in which it is simply defined that the electric fields at different positions are identical to each other, an electromagnetic field analysis of an anisotropic conductive material having anisotropic conductivity can be performed with high accuracy.

Modifications

An implementation to which the present invention is applicable is not limited to the above implementation, and modifications are permissible, as appropriate, so long as they do not depart from the scope of the invention.

For instance, although the anisotropic conductive material to be analyzed is fiber reinforced plastic in the above implementation, the anisotropic conductive material according to the implementation of the present invention is not particularly limited so long as the conductivity in a predetermined first direction is different from that in another direction, and does not have to be fiber reinforced plastic.

The invention claimed is:

1. An electromagnetic field analysis method for an anisotropic conductive material, the electromagnetic field analysis method comprising:
   using an analysis grid having a first side and a second side that are orthogonal to each other is used to analyze an electromagnetic property of the anisotropic conductive material in which conductivity in a first direction is different from conductivity in a second direction,
   wherein one or both of the first direction and the second direction are parallel to a direction different from either one of the first side and the second side of the analysis grid; and
   calculating one electromagnetic field component located on the first side and extending along the second side is calculated based on electromagnetic field components that are located on second sides surrounding the one electromagnetic field component and that extend along the second sides,
   wherein the analysis grid comprises a cubical analysis grid extending along three orthogonal axes, wherein a conductivity tensor obtained when conductivity defined in a coordinate system of the three orthogonal axes is rotated about an axis orthogonal to both of the first direction and the second direction is applied to Ampere's expression and is subsequently discretized by using a finite-difference time-domain method.

2. The electromagnetic field analysis method according to claim 1,
   wherein the one electromagnetic field component is calculated as an average value of the electromagnetic field components.

3. The electromagnetic field analysis method according to claim 1,
   wherein in a case where the one electromagnetic field component is located on the first side extending along a peripheral edge of the anisotropic conductive material, the one electromagnetic field component is calculated based on at least one of the electromagnetic field components included in the anisotropic conductive material.

4. The electromagnetic field analysis method according to claim 2,
   wherein in a case where the one electromagnetic field component is located on the first side extending along a peripheral edge of the anisotropic conductive material, the one electromagnetic field component is calculated based on at least one of the electromagnetic field components included in the anisotropic conductive material.

5. The electromagnetic field analysis method according to claim 1,
   wherein the electromagnetic field components comprise four electromagnetic field components respectively located on four of the second sides coupled to the first side at two nodal points of opposite ends of the first side on which the one electromagnetic field component is located.

6. The electromagnetic field analysis method according to claim 2,
   wherein the electromagnetic field components comprise four electromagnetic field components respectively located on four of the second sides coupled to the first side at two nodal points of opposite ends of the first side on which the one electromagnetic field component is located.

7. The electromagnetic field analysis method according to claim 3,
   wherein the electromagnetic field components comprise four electromagnetic field components respectively located on four of the second sides coupled to the first side at two nodal points of opposite ends of the first side on which the one electromagnetic field component is located.

8. The electromagnetic field analysis method according to claim 4,
   wherein the electromagnetic field components comprise four electromagnetic field components respectively located on four of the second sides coupled to the first side at two nodal points of opposite ends of the first side on which the one electromagnetic field component is located.

9. The electromagnetic field analysis method according to claim 1,
wherein the electromagnetic field analysis method uses the finite-difference time-domain method,
and
wherein when performing calculation repeatedly by applying an iterative method to the discretized expression, an undefined electromagnetic field component included in the discretized expression is calculated as the one electromagnetic field component from the electromagnetic field components.

10. The electromagnetic field analysis method according to claim 2,
wherein the electromagnetic field analysis method uses the finite-difference time-domain method,
and
wherein when performing calculation repeatedly by applying an iterative method to the discretized expression, an undefined electromagnetic field component included in the discretized expression is calculated as the one electromagnetic field component from the electromagnetic field components.

11. The electromagnetic field analysis method according to claim 3,
wherein the electromagnetic field analysis method uses the finite-difference time-domain method,
and
wherein when performing calculation repeatedly by applying an iterative method to the discretized expression, an undefined electromagnetic field component included in the discretized expression is calculated as the one electromagnetic field component from the electromagnetic field components.

12. The electromagnetic field analysis method according to claim 4,
wherein the electromagnetic field analysis method uses the finite-difference time-domain method,
and
wherein when performing calculation repeatedly by applying an iterative method to the discretized expression, an undefined electromagnetic field component included in the discretized expression is calculated as the one electromagnetic field component from the electromagnetic field components.

13. The electromagnetic field analysis method according to claim 1,
wherein the anisotropic conductive material comprises fiber reinforced plastic in which plastic is reinforced with conductive fiber extending in either one of the first direction and the second direction.

14. The electromagnetic field analysis method according to claim 2,
wherein the anisotropic conductive material comprises fiber reinforced plastic in which plastic is reinforced with conductive fiber extending in either one of the first direction and the second direction.

15. The electromagnetic field analysis method according to claim 3,
wherein the anisotropic conductive material comprises fiber reinforced plastic in which plastic is reinforced with conductive fiber extending in either one of the first direction and the second direction.

16. The electromagnetic field analysis method according to claim 4,
wherein the anisotropic conductive material comprises fiber reinforced plastic in which plastic is reinforced with conductive fiber extending in either one of the first direction and the second direction.

17. The electromagnetic field analysis method according to claim 1, further comprising modifying the electromagnetic property of the anisotropic conductive material based on a result of the analysis using the analysis grid.

18. An electromagnetic field analysis method for an anisotropic conductive material, the electromagnetic field analysis method comprising:
creating an analysis grid having a first side and a second side that are orthogonal to each other to analyze an electromagnetic property of the anisotropic conductive material in which conductivity in a first direction is different from conductivity in a second direction, one or both of the first direction and the second direction being parallel to a direction different from either one of the first side and the second side of the analysis grid;
calculating one electromagnetic field component located on the first side and extending along the second side based on electromagnetic field components that are located on second sides surrounding the one electromagnetic field component and that extend along the second sides; and
modifying the electromagnetic property of the anisotropic conductive material based on a result of the analysis using the analysis grid.

* * * * *